United States Patent [19]

Asato

[11] 4,053,484
[45] Oct. 11, 1977

[54] 1-BENZOYL-3-(4,5,6,7-TETRAHYDROBENZO[b]THIEN-4-YL)UREAS AND 1-BENZOYL-3-(4,5,6,7-TETRAHYDRO-7-OXOBENZO[b]THIEN-4-YL)UREAS, NOVEL INTERMEDIATES FOR THE PREPARATION OF ANIMAL GROWTH PROMOTING AGENTS

[75] Inventor: Goro Asato, Titusville, N.J.

[73] Assignee: American Cyanamid Company, Stamford, Conn.

[21] Appl. No.: 691,801

[22] Filed: June 1, 1976

Related U.S. Application Data

[63] Continuation-in-part of Ser. No. 532,449, Dec. 13, 1974, abandoned, which is a continuation-in-part of Ser. No. 436,827, Jan. 25, 1974, abandoned.

[51] Int. Cl.$^2$ ................ C07D 333/16; A01N 9/00
[52] U.S. Cl. ................ 260/332.3 P; 260/329 AM; 260/329 F; 424/275
[58] Field of Search ................ 260/332.3 P

[56] References Cited

U.S. PATENT DOCUMENTS 3,705,910  12/1972  Lundberg et al. ............... 260/332.3

Primary Examiner—James O. Thomas, Jr.
Assistant Examiner—A. Siegel
Attorney, Agent, or Firm—Edward A. Conroy, Jr.

[57] ABSTRACT

This invention relates to 1-benzoyl-3-(4,5,6,7-tetrahydrobenzo[b]thien-4-yl)urea, 1-benzoyl-3-(4,5,6,7-tetrahydro-7-oxobenzo[b]thien-4-yl)urea, and derivatives thereof and a method for the preparation of said compounds and substituted derivatives. Both of the above referred-to compounds are novel and useful intermediates for the preparation of the corresponding tetrahydrobenzo[b]thien-4-ylurea and tetrahydro-7-oxobenzo[b]thien-4-ylurea, respectively. The latter compounds and certain derivatives thereof are animal growth promoting agents.

6 Claims, No Drawings

1-BENZOYL-3-(4,5,6,7-TETRAHYDROBENZO [b]THIEN-4-YL)UREAS AND 1-BENZOYL-3-(4,5,6,7-TETRAHYDRO-7-OXOBENZO [b]THIEN-4-YL)UREAS, NOVEL INTERMEDIATES FOR THE PREPARATION OF ANIMAL GROWTH PROMOTING AGENTS

CROSS REFERENCE TO RELATED APPLICATIONS

This application is a continuation-in-part of my copending application Ser. No. 532,449, filed Dec. 13, 1974 now abandoned which is a continuation-in-part of my abandoned application Ser. No. 436,827, filed Jan. 25, 1974 now abandoned.

BRIEF SUMMARY OF THE INVENTION

This invention relates to novel compounds of the formula:

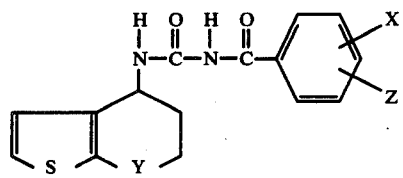

(I)

wherein X is selected from hydrogen, methyl, methoxy, chloro and nitro; Z is selected from hydrogen, chloro and nitro; Y is selected from

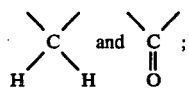

and said compounds may be the racemic mixtures or the optically active isomers thereof.

This invention also relates to methods for the preparation of the above-identified formula (I) compounds, which may be the racemic mixtures or the optically active isomers thereof.

DETAILED DESCRIPTION OF THE INVENTION

In accordance with this invention, a formula (I) compound, wherein Y is selected from

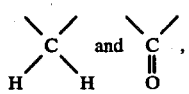

can be prepared by reacting the corresponding thiophen-4-amine of formula (II), or an acid addition salt thereof, with benzoyl (or a substituted benzoyl) isocyanate as hereinbelow graphically illustrated:

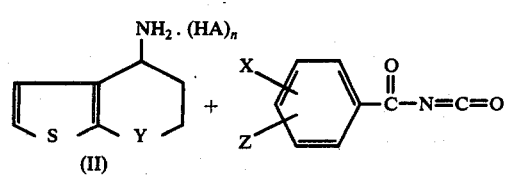

wherein X is selected from hydrogen, methyl, methoxy, chloro and nitro; Z is selected from hydrogen, chloro and nitro; Y is selected from $$\begin{array}{cc} \diagdown \diagup & \diagdown \diagup \\ C & \text{and} & C \\ \diagup \diagdown & \parallel \\ H \quad H & O \end{array}$$

HA represents an acid selected from hydrochloric, hydrobromic and hydriodic acid; $n$ is 0 or 1; and said formulae (I) and (II) compounds are the racemic mixtures or the optical isomers thereof.

The reaction can be carried out using approximately equimolar amounts of a formula (II) amine or an acid addition salt thereof and benzoyl (or a substituted benzoyl) isocyanate; however, it is generally preferable to employ from 5 % to 50% excess of the isocyanate. The reaction can be conducted at atmospheric or superatmospheric pressure at a temperature in the range of 0° to 100° C, but is preferably conducted at atmospheric pressure in the presence of an organic solvent.

Suitable organic solvents include aprotic aromatic solvents such as benzene, toluene and xylene; chlorinated hydrocarbon solvents such as methylene chloride, chloroform and dichloroethane; ethers such as tetrahydrofuran, diethyl ether, dimethoxyethane, diethylene glycol dimethyl ether and dioxane; lower alkyl $C_1$–$C_4$ ketones such as acetone, methyl ethyl ketone, methyl butyl ketone and methyl isobutyl ketone, or mixtures of said solvents.

When the above reaction is carried out using a formula (II) amine acid addition salt, it is desirable to add an acid acceptor to the reaction mixture. Suitable acid acceptors include trialkylamines such as triethylamine, trimethylamine, pyridine or the like; alkali metal carbonates such as sodium or potassium carbonate; alkaline earth metal carbonates such as calcium carbonate; and strong basic ion exchange resins, and aqueous alkali in a 2-phase system using an immiscible solvent, such as benzene or toluene, or a chlorinated hydrocarbon, such as chloroform or dichloroethane.

The above reaction may be graphically illustrated, in detail, as follows:

A. When Y is $\begin{array}{c} \diagdown \diagup \\ C \\ \diagup \diagdown \\ H \quad H \end{array}$

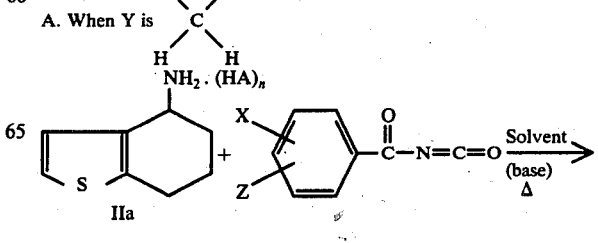

-continued

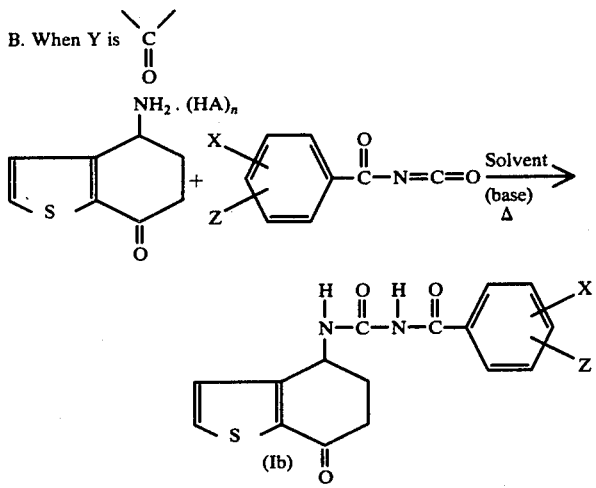

wherein X, Z, HA and n are as hereinabove defined.

Hydrolysis of formulae (Ia) and (Ib) compounds in acidic or alkaline medium, preferably an aqueous alkaline environment yields the corresponding thien-4-ylureas of formulae (IIIa) and (IIIb) wherein said compounds, as stated above, are animal growth promoting agents. The above reaction may be graphically illustrated as follows:

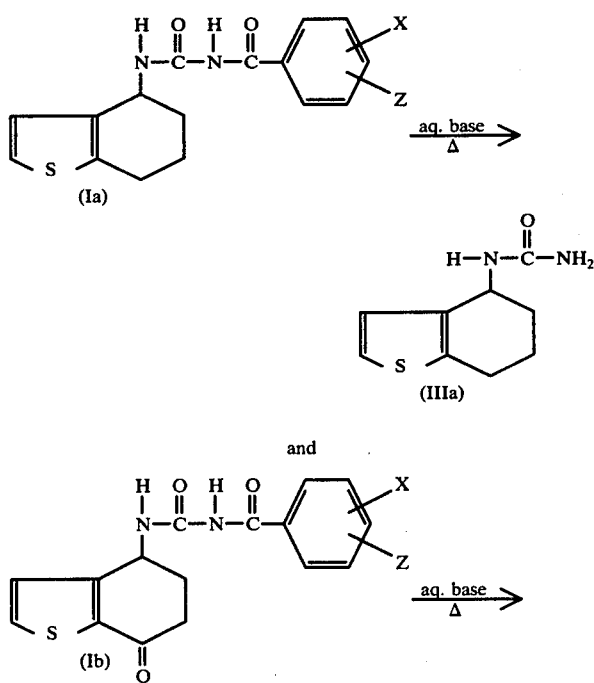

-continued

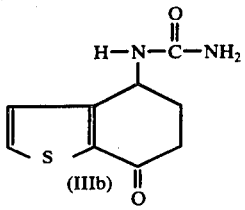

It is recognized, of course, that other groups hereinabove not mentioned, and removable by hydrolysis, may be substituted for the above defined benzoyl group to yield useful intermediates for the preparation of compounds of formulae (IIIa) and (IIIb); nevertheless the use of said benzoyl group for this purpose is novel and hitherto undisclosed.

The intermediate 4,5,6,7-tetrahydro-7-oxobenzo[b]-thiolphen-4-amine of formula (IIb) can be prepared by an oxidation reaction, comprising reacting one equivalent of a compound of formula (IV) with 2 to 8 equivalents and preferable 4 to 5 equivalents of an oxidizing agent selected from the group consisting of ceric ammonium nitrate, ceric sulfate, chromic anhydride, sodium bichromate, silver oxide and the like, at a temperature between about 0° and 100° C, and preferably 20° to 60° C, in a solvent selected from aqueous solutions of acetic acid, acetonitrile, tetrahydrofuran, dioxane, dimethoxyethane, diethylene glycol dimethyl ether, which may contain nitric acid, phosphoric acid or perchloric acid, or with the oxidizing agent chromic anhydride in acetic anhydride followed by hydrolysis. The above reaction may be graphically illustrated as follows:

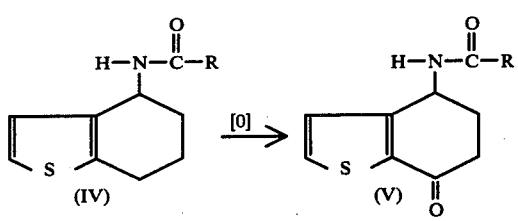

wherein R is hydrogen or alkyl $C_1$-$C_4$. On completion of the oxidation step, the resulting formula (V) oxo compound is hydrolyzed in an aqueous mineral acid to afford the acid addition salt of formula (II) 4,5,6,7-tetrahydro-7-oxobenzo-[b]thiophen-4-amine. Substitution of an aqueous base (e.g. sodium hydroxide) for the above aqueous acid affords also the formula (II) amine.

Conveniently, the above oxidation procedure can be utilized to convert a benzoylurea compound of formula (Ia) to a compound of formula (Ib) as hereinbelow graphically illustrated:

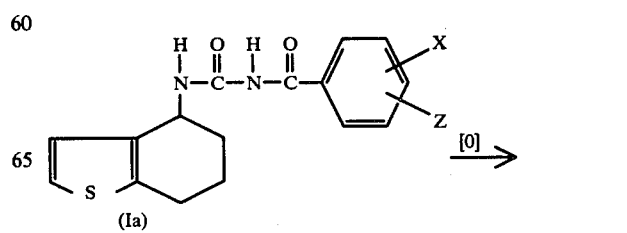

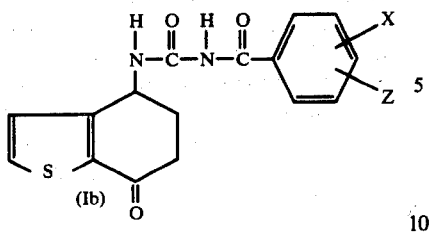

(Ib)

wherein X and Z are as defined above with the proviso that X and Y are not methyl and said compounds are the racemic mixtures and the optical isomers thereof. Hydrolysis of a formula (Ib) compound yields the animal growth promoter of formula (IIIb): 4,5,6,7-tetrahydro-7-oxo-benzo[b]thien-4-yl-urea; the racemic mixture and the optical isomers thereof.

All of the above preparations leading to the novel compounds of formulae (Ia) and (Ib) and ultimately to the animal growth promoting agents of formulae (IIIa) and (IIIb) yield racemic (dl) mixtures.

Should the optically active isomers be desired, these may be prepared by the hereinabove described procedures, using the corresponding resolved, optically active 4,5,6,7-tetrahydrobenzo [b]thiophen-4-amine or its 7-oxo derivative, respectively.

The preparation of the optically active 4,5,6,7-tetrahydrobenzo[b]thiophen-4-amine for the synthesis of the novel compounds of the present invention, represented and defined by formula (I) above may be accomplished as follows. The racemic (dl) 4,5,6,7-tetrahydrobenzo[b]thiophen-4-amine is treated with (+)-N-benzoylglutamic acid to form a water-insoluble salt of (+)-4,5,6,7-tetrahydrobenzo[b]thiophen-4-amine in high yield. It is not necessary to employ more than one mole of the resolving acid for each two moles of dl amine, as a cheaper acid, preferably acetic acid, can be substituted for the balance of the required acid. In this way it is possible to obtain a high yield of the desired (+)-amine based on the resolving acid. The resolved salt, (+)-4,5,6,7-tetrahydrobenzo[b]thiophen-4-amine (+)-N-benzoylglutamic acid, is treated with alkali which liberates the (+)-amine which separates as an insoluble phase. It can be mechanically separated from the aqueous phase or extracted conventionally with a suitable solvent.

The (−)-amine which remains in solution is then recovered and treated with (−)-N-benzoylglutamic acid and acetic acid in the above-mentioned manner with the molarity adjusted to the amount of (+)-amine obtained from the initial resolution. The salt, (−)-4,5,6,7-tetrahydrobenzo[b]thiophen-4-amine · (−)-N-benzoylglutamic acid, crystallizes and is then treated in the above-mentioned manner to give the (−)-amine.

Because 4,5,6,7-tetrahydro-7-oxobenzo[b]thiophen-4-amine is also a useful intermediate, this compound in its optically active form is desirable. Thus, dl-4,5,6,7-tetrahydro-7-oxobenzo[b]thiophen-4-amine is readily resolved with (+)-tartaric acid in methanol as follows:

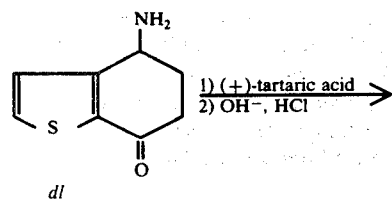

dl

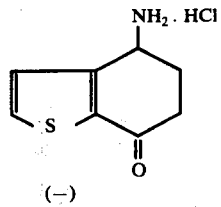

(−)

and the resulting crystalline tartrate salt is recrystallized from 95% ethanol. The salt is decomposed with aqueous NaOH solution and the optically active keto-amine is separated by conventional extraction and acidified with HCl to afford (−)-4,5,6,7-tetrahydro-7-oxobenzo[b]thiophen-4-amine hydrochloride, which can be used in the manner described above.

As hereinabove mentioned, 4,5,6,7-tetrahydrobenzo[b]thien-4-ylurea of formula (IIIa) and 4,5,6,7-tetrahydro-7-oxobenzo[b]thien-4-ylurea of formula (IIIb) are useful as growth promoting agents for farm animals such as cattle, sheep, horses, swine, fur-bearing animals such as foxes, rabbits, minks and the like and companion animals such as dogs and cats.

In practice, a growth-promoting amount of a formula (IIIa) or a formula (IIIb) thienylurea, or an optically active isomer thereof, is administered to the host animal usually in, or with, the animals's feed. When administered in the feed, usually about 0.0001% to 0.08% by weight, and preferably 0.001% to 0.04% by weight of a formula (IIIa) or formula (IIIb) thienylurea, is effective for increasing growth rate.

However, said compounds may also be administered as one or more subcutaneous implant(s) under the skin of said animal or as a parenteral injection. When administered to said animals as a subcutaneous implant or parenteral injection, usually in amounts that will supply about 0.0005 mg to 0.20 mg and preferably 0.001 mg to 0.10 mg per kg of body weight per day of the active compound, will produce the desired improvement in weight gain.

The present invention is further illustrated by the non-limiting examples set forth below.

EXAMPLE 1

Preparation of 1-benzoyl-3-(4,5,6,7-tetrahydrobenzo[b]thien-4-yl)urea

A solution of benzoyl isocyanate (2.94g) in methylene chloride (5ml) is added to a solution of 4,5,6,7-tetrahydrobenzo[b]thiophen-4-amine is methylene chloride (50ml) under a nitrogen atmosphere. After stirring overnight at room temperature, the reaction mixture is evaporated to dryness in vacuo. The residue is then stirred in ether (100ml) and filtered to afford 1-benzoyl-3-(4,5,6,7-tetrahydrobenzo-[b]thien-4-yl)urea, m.p. 189° to 194° C.

In the same manner, (+)-4,5,6,7-tetrahydrobenzo[b]thiophen-4-amine is used in place of dl 1-4,5,6,7-tetrahydrobenzo[b]thiophen-4-amine to afford the optically active title compound.

Similarly, substituted (X,Z)-benzoyl isocyanates are used in place of benzoyl isocyanate to afford the corresponding 1-(substituted benzoyl)-3-(4,5,6,7-tetrahydrobenzo[b]thien-4-yl) ureas as follows:

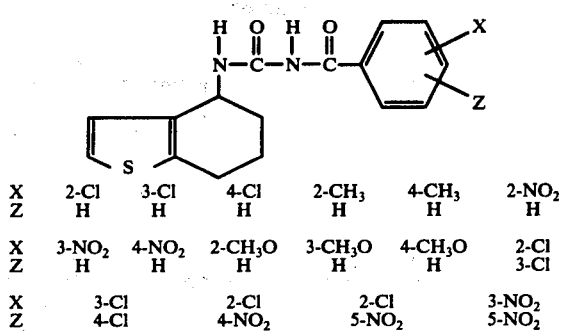

| X | 2-Cl | 3-Cl | 4-Cl | 2-CH₃ | 4-CH₃ | 2-NO₂ |
|---|---|---|---|---|---|---|
| Z | H | H | H | H | H | H |

| X | 3-NO₂ | 4-NO₂ | 2-CH₃O | 3-CH₃O | 4-CH₃O | 2-Cl |
|---|---|---|---|---|---|---|
| Z | H | H | H | H | H | 3-Cl |

| X | 3-Cl | 2-Cl | 2-Cl | 3-NO₂ |
|---|---|---|---|---|
| Z | 4-Cl | 4-NO₂ | 5-NO₂ | 5-NO₂ |

The substituted benzoyl isocyanates used above, are readily prepared by reacting the corresponding benzamides with oxalyl chloride in ethylene dichloride by the method of Speziale and Smith [J. Org. Chem., 28, 1805(1963)].

EXAMPLE 2

Preparation of 4,5,6,7-Tetrahydrobenzo[b]thien-4-ylurea

A mixture of 1-benzoyl-3-(4,5,6,7-tetrahydrobenzo[b]thien-4-yl) urea and 2N aqueous sodium hydroxide solution (5ml) is stirred at reflux for 2.5 hours. The mixture is cooled in ice, the product is collected and washed with water to afford 0.58 g of title compound, m.p. 203° to 207° C.

Similarly, 1-(2-chlorobenzoyl)-, 1-(3-chlorobenzoyl)-, 1-(4-chlorobenzoyl)-, 1-(2-methylbenzoyl)-, 1-(3-methylbenzoyl)-, 1-(4-methylbenzoyl)-, 1-(2-nitrobenzoyl)-, 1-(3-nitrobenzoyl)-, 1-(4-nitrobenzoyl)-, 1-(2-methoxybenzoyl)-, 1-(3-methoxybenzoyl)-, 1-(4-methoxybenzoyl)-, 1-(2-chloro-4-nitrobenzoyl)-, 1-(2-chloro-5-nitrobenzoyl)-, 1-(2,4-dichlorobenzoyl)-, 1-(3,4-dichlorobenzoyl)- and 1-(3,5-dinitrobenzoyl)- 3-(4,5,6,7-tetrahydrobenzo[b]thien- 4-yl)urea, respectively, are substituted for 1-benzoyl-3-(4,5,6,7-tetrahydrobenzo[b]thien- 4-ylurea to afford the title compound.

EXAMPLE 3

Preparation of N-(4,5,6,7-tetrahydro-7-oxobenzo[b]thien-4-yl)acetamide

A solution of N-(4,5,6,7-tetrahydrobenzo[b]thien-4,yl)acetamide (137.8 g) in a mixture of water (1400 ml) and glacial acetaic acid (170 ml) is cooled to -5° C. The solution is stirred and ceric ammonium nitrate (1550 g) added in portions over 0.5 hour. The temperature of the reaction mixture is kept at 10° to 15° C and then the solution is stirred at room temperature for 0.5 hour. Solid sodium sulfate (602 g) is then added and after stirring for 1.5 hours, the mixture is filtered. The filtrate is extracted with methylene chloride (3×1000 ml), the extracts are combined and washed with brine. The combined extracts are then evaporated to dryness in vacuo to afford a solid, which is then stirred with ether (755 ml) and filtered to yield the insoluble title compound (124.6 g).

EXAMPLE 4

Preparation of 4,5,6,7-Tetrahydro-7-oxobenzo[b]thiophen-4-amine

A mixture of N-(4,5,6,7-tetrahydro-7-oxobenzo[b]thien-4-yl)acetamide (16.0 g), water (100 ml) and concentrated hydrochloric acid (100 ml) is stirred and heated at reflux for an overnight period. The mixture is cooled, made alkaline with 50% aqueous sodium hydroxide, and saturated with sodium chloride. The mixture is then extracted with methylene chloride (3×250 ml). The extracts are combined, dried over magnesium sulfate and then evaporated to dryness in vacuo to afford the title compound as a yellow-brown syrup.

EXAMPLE 5

Preparation of 1-Benzoyl-3-(4,5,6,7-tetrahydro-7-oxobenzo[b]-thien-4-yl)urea

A solution of 4,5,6,7-tetrahydro-7-oxobenzo[b]thiophen-4-amine (8.02 g) in methylene chloride (75 ml) is added to a stirred solution of benzoyl isocyanate (7.0 g) in methylene chloride (75 ml) under a nitrogen atmosphere. The mixture is stirred for an overnight period at room temperature and the title compound is collected by filtration. Recrystallization of the crude product from acetone/hexane affords 5.7 g of the title compound, m.p. 204° to 207° C.

Similarly, benzoyl isocyanate is replaced by substituted (X,Z)-benzoyl isocyanates to afford the following 1-(substituted-benzoyl)-3-(4,5,6,7-tetrahydro-7-oxobenzo[b]-thien- 4-yl)ureas;

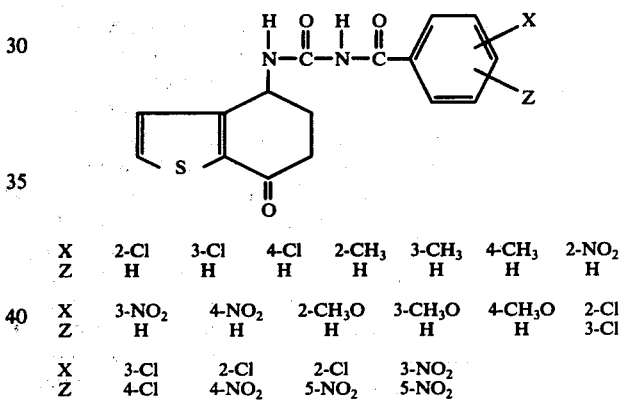

| X | 2-Cl | 3-Cl | 4-Cl | 2-CH₃ | 3-CH₃ | 4-CH₃ | 2-NO₂ |
|---|---|---|---|---|---|---|---|
| Z | H | H | H | H | H | H | H |

| X | 3-NO₂ | 4-NO₂ | 2-CH₃O | 3-CH₃O | 4-CH₃O | 2-Cl |
|---|---|---|---|---|---|---|
| Z | H | H | H | H | H | 3-Cl |

| X | 3-Cl | 2-Cl | 2-Cl | 3-NO₂ |
|---|---|---|---|---|
| Z | 4-Cl | 4-NO₂ | 5-NO₂ | 5-NO₂ |

EXAMPLE 6

Preparation of 4,5,6,7-Tetrahydro-7-oxobenzo[b]thien-4-yl-urea

A mixture of 1-benzoyl-3-(4,5,6,7-tetrahydro-7-oxobenzo[b]thien-4-yl)urea (3.0 g) and 1N sodium hydroxide (10ml) is stirred and heated at reflux for 6 hours. Additional 1N sodium hydroxide (5 ml) is then added and the mixture heated for another hour. The mixture is then cooled to room temperature and the title compound is collected by filtration and washed well with water. The title compound is dried to afford 1.71 g, m.p. 241° to 244° C.

Similarly, replacing 1-benzoyl-3-(4,5,6,7-tetrahydro-7-oxobenzo[b]thien-4-yl)urea with 1-(2-chlorobenzoyl)-, 1-(3-chlorobenzoyl)-, 1-(4-chlorobenzoyl)-, 1-(2-nitrobenzoyl)-, 1-(3-nitrobenzoyl)-, 1-(4-nitrobenzoyl)-, 1-(2-methylbenzoyl)-, 1-(3-methylbenzoyl)-, 1-(4-methylbenzoyl)-, 1-(2-methoxybenzoyl)-, 1-(3-methoxybenzoyl)-, 1-(4-methoxybenzoyl)-, 1-(2-chloro-4-nitrobenzoyl)-, 1-(2-chloro- 5-nitrobenzoyl)-, 1-(2,4-dichlorobenzoyl)-, 1-(3,4-dichlorobenzoyl)- and 1-(3,5-dinitrobenzoyl)-3-(4,5,6,7-tetrahydro-7-oxobenzo-

[b]thien-4-yl)urea, respectively, affords the title compound.

EXAMPLE 7

Mouse Growth Regulant Tests

CFI female mice from Carworth Farm are received when they are 6 weeks old. They are housed 10 to a cage in air-conditioned rooms (72° to 76° F) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of 10 and assigned at random to the different treatments. The concentration of the different compounds in the diet is indicated in the following Table. Twelve days later the mice are weighed again and the experiment terminated. At least 3 cages (30 mice) of untreated controls are included in each test. Test data are provided in Table I below wherein data are reported as percent weight gain over controls. The following is a description of the diet to which the growth promoting compounds are added.

DIET

GUARANTEED ANALYSIS

| | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, can molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

Table I

Effectiveness of Tetrahydrobenzo[b]thienylurea compounds of formula (I) as Animal Growth Promoting Agents Reported as Percent Weight Gain Over Controls Using Mice as the Test Animal (I)

| Rate ppm in Diet | Y | % Weight Gain Over Control | Remarks |
|---|---|---|---|
| 50 | \C/ with H, H | 50.1 | racemic |
| 200 | \C/ with H, H | 134.2 | racemic |
| 400 | \C/ with H, H | 119.6 | racemic |
| 400 | \C=O | 134 | racemic |
| 25 | \C=O | 135 | levorotatory |

EXAMPLE 8

Preparation of (−)-4,5,6,7-tetrahydro-7-oxobenzo[b]thien-4-ylurea

A sample of 1.02 g of (dl-1-4,5,6,7-tetrahydro-7-oxobenzo[b]thiophen-4-amine hydrochloride is treated with 0.8 g of sodium hydroxide in 13 ml of water and the free amine is extracted with chloroform several times (total volume 200 ml.) The chloroform extract is washed with brine, dried over $Na_2SO_4$ under nitrogen atmosphere, and the solution is evaporated to dryness to afford the liquid amine. The amine is dissolved in 5 ml of methanol and a solution of 0.75 g of (+)-tartaric acid in 10 ml of methanol is added. The mixture is warmed slightly and allowed to cool to room temperature. The crystals are collected and fractionally crystallized from 85–90 ml of 95% ethanol to afford 0.6 g of salt. This salt is treated with 0.8 g of NaOH in 13 ml of water and the mixture is extracted several times with $CHCl_3$ (total volume 200 ml). The combined extracts are washed with brine, dried over $Na_2SO_4$ under nitrogen and the solution is evaporated to dryness. The residual amine is dissolved in 10 ml of acetone and treated with a saturated solution of HCl in isopropyl alcohol (1–2 ml) until solid no longer forms. The solid amine hydrochloride is collected and dried; m.p. 219° to 221° C (dec.); $[\alpha]_D^{28} = -14.32°$ C (c, 0.91 in methanol).

The amine hydrochloride is stirred in water and the mixture is made alkaline. The amine is then extracted with methylene chloride, dried over magnesium sulfate, filtered, and added to a methylene chloride solution of benzoyl isocyanate. The workup is completed as in Example 5. Alkaline hydrolysis of the 1-benzoyl-3-(4,5,6,7-tetrahydro-7-oxobenzo-[b]thien-4-yl)urea is accomplished by the method given in Example 6 to afford (−)-4,5,6,7-tetrahydro-7-oxobenzo[b]thien-4-ylurea.

I claim:

1. dl-1-Benzoyl-3-(4,5,6,7-tetrahydrobenzo-[b]-thien-4-yl)urea.

2. d-1-Benzoyl-3-(4,5,6,7-tetrahydrobenzo-[b]-thien-4-yl)urea.

3. *l*-1-Benzoyl-3-(4,5,6,7-tetrahydrobenzo-[*b*]-thien-4-yl)urea.

4. *dl*-1-Benzoyl-3-(4,5,6,7-tetrahydro-7-oxobenzo-[*b*]-thien-4-yl)urea.

5. *d*-1-Benzoyl-3-(4,5,6,7-tetrahydro-7-oxobenzo-[*b*]-thien-4-yl)urea.

6. *l*-1-Benzoyl-3-(4,5,6,7-tetrahydro-7-oxobenzo-[*b*]-thien-4-yl)urea.